US006316044B2

(12) United States Patent
Ottersbach et al.

(10) Patent No.: US 6,316,044 B2
(45) Date of Patent: Nov. 13, 2001

(54) PROCESS FOR THE PREPARATION OF ANTIMICROBIAL ARTICLES

(75) Inventors: Peter Ottersbach, Windeck; Frank Hill, *deceased*, late of Mettmann, by Hella Luise Hill, Henning Hinrich Hill, Friedrich Frank Hill, Regina Luise Hill; Christine Anders, Haltern, all of (DE)

(73) Assignee: Degussa-Huels Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/527,829

(22) Filed: Mar. 17, 2000

Related U.S. Application Data

(63) Continuation of application No. 09/036,194, filed on Mar. 6, 1998, now Pat. No. 6,096,800.

(30) Foreign Application Priority Data

Mar. 6, 1997 (DE) .............................................. 197 09 076

(51) Int. Cl.$^7$ ...................................................... A61L 13/00
(52) U.S. Cl. ........................ 427/2.31; 427/223; 427/299; 427/322; 427/325; 427/327; 427/385.5; 427/388.1; 427/393; 427/393.5; 427/399; 427/421; 427/430.1; 427/440; 427/443.2; 427/488; 427/496; 427/498; 427/512; 427/535; 427/551; 427/553; 427/558; 427/559; 427/569; 427/580; 427/595

(58) Field of Search ..................................... 427/488, 496, 427/498, 512, 535, 551, 553, 558, 2.31, 559, 569, 385.5, 388.1, 393, 393.5, 325, 327, 322, 299, 421, 399, 223, 580, 595, 440, 443.2, 430.1

(56) References Cited

U.S. PATENT DOCUMENTS 4,273,690 * 6/1981 Walus .
5,967,714   10/1999 Ottersbach et al. .

* cited by examiner

*Primary Examiner*—Bernard Pianalto
(74) *Attorney, Agent, or Firm*—Oblon, Spivak, McClelland, Maier & Neustadt, P.C.

(57) ABSTRACT

Antimicrobial activity is imparted to the surface(s) of an apparatus or article by polymerizing tert-butylaminoethyl methacrylate in the presence of the apparatus or article by which adhesion of the polymer to the surface(s) is achieved. In a preferred embodiment of the invention the antimicrobial monomer is graft polymerized on the surface(s).

5 Claims, No Drawings

PROCESS FOR THE PREPARATION OF ANTIMICROBIAL ARTICLES

This application is a continuation of application Ser. No. 09/036,194, filed on Mar. 6, 1998, U.S. Pat. No. 6,096,800.

BACKGROUND OF THE INVENTION

1. Field of the Invention

The present invention relates to a process for the preparation of antimicrobial polymers by polymerization of tert-butylaminoethyl methacrylate, and the use of the antimicrobial polymers. More particularly, the invention relates to a process for the preparation of antimicrobial polymers by graft polymerization of tert-butylaminoethyl methacrylate on a substrate, and the use of the antimicrobial polymers.

2. Description of the Background

The colonization and spread of bacteria on surfaces of pipelines, containers or packaging is highly undesirable. Layers of slime often form, which allow the microbe populations to rise to extreme levels, lastingly impairing the quality of water, drinks and foodstuffs, and can even lead to decay of the goods and damage to the health of consumers.

Bacteria are to be kept away from all areas of life where hygiene is of importance. Since textiles directly contact the body, and, in particular the genital area, and are used for the care of the sick and elderly, textiles should be freed of bacteria. Bacteria should also be kept away from the surfaces of furniture and equipment in nursing wards, in particular in the intensive care and infant care sector, in hospitals, especially in rooms for medical operations, and in isolation wards for critical cases of infection, as well as in toilets.

Equipment, and surfaces of furniture and textiles are currently treated to ward against bacteria as required or also preventively with chemicals or solutions and mixtures thereof which act as disinfectants, such having a more or less broad and powerful antimicrobial action. Such chemical compositions have a nonspecific action, are often themselves toxic or irritating, or form degradation products which are unacceptable to health. Intolerances are often also found in appropriately sensitized persons. Another procedure which is used to inhibit the spread of bacteria on surfaces is to incorporate antimicrobially active substances into a matrix.

Tert-butylaminoethyl methacrylate is a commercially available monomer of methacrylate chemistry and is employed in particular as a hydrophilic monomer in copolymerizations. Thus, EP 0 290 676 describes the use of various polyacrylates and polymethacrylates as a matrix for immobilization of bactericidal quaternary ammonium compounds.

U.S. Pat. No. 3,592,805 discloses the preparation of systemic fungicides in which per halogenated acetone derivatives are reacted with methacrylate esters, such as, for example, tert-butylaminoethyl methacrylate.

U.S. Pat. No. 4,515,910 describes the use of polymers of hydrogen fluoride salts of aminomethacrylates in dental medicine. The hydrogen fluoride bonded in the polymers emerges slowly from the polymer matrix and is said to be effective against caries.

In another technical field, U.S. Pat. No. 4,532,269 discloses a terpolymer of butyl methacrylate, tributyltin methacrylate and tert-butylaminoethyl methacrylate. This polymer is used as an antimicrobial paint for ships, the hydrophilic tert-butylaminoethyl methacrylate promoting slow erosion of the polymer and in this way liberating the highly toxic tributyltin methacrylate as an antimicrobially active compound.

In these applications, the copolymer prepared with aminomethacrylates is only a matrix or carrier substance for added microbicidal active compounds, which can diffuse or migrate out of the carrier. Polymers of this type lose their action at a faster or slower rate when the necessary "minimum inhibitory concentration" (MIC) is no longer achieved on the surface.

EP 0 204 312 describes a process for the preparation of antimicrobially treated acrylonitrile fibers. The antimicrobial action is based on a protonated amine as a comonomer unit, dimethylaminoethyl methacrylate and tertbutylaminoethyl methacrylate, inter alia, being used as protonated species. However, the antimicrobial action of protonated surfaces is severely reduced after loss of the H(+) ions. A need continues to exist for an effective method of providing surfaces of objects with antimicrobial properties.

SUMMARY OF THE INVENTION

Accordingly, one object of the present invention is to provide materials which have antimicrobial properties, which contain no active compounds which can be washed out, and in which the antimicrobial action is pH-independent.

Another object of the present invention is to provide surfaces of objects and apparatus with a permanently microbicidal polymeric coating which is not attacked by solvents and physical stress and which shows no migration, and by which it is not necessary to employ additional biocidally active compounds.

Briefly, these objects and other objects of the present invention as hereinafter will become more readily apparent can be attained by a method of imparting antimicrobial activity to the surface(s) of an apparatus or article, which comprises polymerizing tert-butylaminoethyl methacrylate in the presence of the apparatus or article by which adhesion of the polymer to said surface(s) is achieved. In a preferred embodiment of the invention the tert-butylaminoethyl methacrylate monomer is graft polymerized onto the surface.

DETAILED DESCRIPTION OF THE PREFERRED EMBODIMENTS

The antimicrobial polymers of the invention can be obtained by grafting polymerizing tert-butylaminoethyl methacrylate on a surface of an article or apparatus.

Suitable substrate materials include, above all, all polymeric plastics, such as, for example, polyurethanes, polyamides, polyesters, polyethers, polyether-block amides, polystyrene, polyvinyl chloride, polycarbonates, polyorganosiloxanes, polyolefins, polysulfones, polyisoprene, polychloroprene, polytetrafluoroethylene (PTFE), corresponding copolymers and blends, as well as natural and synthetic rubbers, with or without radiation-sensitive groups. The process of the invention can also be applied on the surfaces of metal, glass or wooden bodies which are painted or are otherwise coated with plastic.

The surfaces of the substrates can be activated by a number of methods before the grafting polymerization. They are expediently freed from oils, greases or other impurities beforehand in a known manner by means of a solvent.

The standard polymers can be activated by UV radiation. A suitable source of radiation is, for example, a UV-Excimer apparatus HERAEUS Noblelight, Hanau, Germany.

However, mercury vapor lamps are also suitable for activation of the substrate if they emit considerable proportions of radiation in the ranges mentioned. The exposure time generally ranges from 0.1 second to 20 minutes, preferably 1 second to 10 minutes.

The activation of the standard polymers with UV radiation can furthermore be carried out with an additional photosensitizer. Suitable such photosensitizers include, for example, benzophenone, as such are applied to the surface of the substrate and irradiated. In this context, irradiation can be conducted with a mercury vapor lamp using exposure times of 0.1 second to 20 minutes, preferably 1 second to 10 minutes.

According to the invention, the activation can also be achieved by a high frequency or microwave plasma (Hexagon, Technics Plasma, 85551 Kirchheim, Germany) in air or a nitrogen or argon atmosphere. The exposure times generally range from 30 seconds to 30 minutes, preferably 2 to 10 minutes.

The energy output of laboratory apparatus is between 100 and 500 W, preferably between 200 and 300 W.

Corona apparatus (SOFTAL, Hamburg, Germany) can furthermore be used for the activation. In this case, the exposure times are, as a rule, 1 to 10 minutes, preferably 1 to 60 seconds.

Activation by electron beams or y-rays, for example, from a cobalt-60 source) and ozonization allow short exposure times which are generally range from 0.1 to 60 seconds.

The flaming of surfaces likewise leads to activation of the surfaces. Suitable apparatus, in particular those having a barrier flame front, can be constructed in a simple manner or obtained, for example, from ARCOTEC, 71297 Mnsheim, Germany. The apparatus can employ hydrocarbons or hydrogen as the combustible gas. In all cases, harmful overheating of the substrates must be avoided, which is easily achieved by intimate contact with a cooled metal surface on the substrate surface facing away from the flaming side. Activation by flaming is accordingly limited to relatively thin, flat substrates. The exposure times generally range from 0.1 second to 1 minute, preferably 0.5 to 2 seconds. The flames without exception are nonluminous and the distances between the substrate surfaces and the outer flame front ranges from 0.2 to 5 cm, preferably 0.5 to 2 cm.

The substrate surfaces activated in this way are coated with tertbutylaminoethyl methacrylate, if appropriate in solution, by known methods, such as by dipping, spraying or brushing. Suitable solvents have proved to be water and water/ethanol mixtures, although other solvents can also be used if they have a sufficient dissolving power for tert-butylaminoethyl methacrylate and wet the substrate surfaces thoroughly. Solutions having monomer contents of 1 to 10% by weight, for example about 5% by weight, have proved suitable in practice and in general give continuous coatings which cover the substrate surface and have coating thicknesses which can be more than 0.1 μm in one pass.

The grafting copolymerization of the monomer applied to the activated surfaces is expediently effected by short wavelength radiation in the visible range or in the long wavelength segment of the UV range of electromagnetic radiation. The radiation of a UV-Excimer of wavelengths 250 to 500 nm, preferably 290 to 320 nm, for example, is particularly suitable. Mercury vapor lamps are also suitable here if they emit considerable amounts of radiation in the ranges mentioned. The exposure times generally range from 10 seconds to 30 minutes, preferably 2 to 15 minutes.

Poly-tert-butylaminoethyl methacrylate also shows intrinsic microbicidal properties without grafting to a substrate surface.

One possible embodiment of the present invention comprises a procedure in which the polymerization of tert-butylaminoethyl methacrylate can be carried out on a substrate.

An antimicrobial polymer can furthermore be prepared by polymerization of tert-butylaminoethyl methacrylate by known processes.

In the process of the invention, the polymer of tert-butylaminoethyl methacrylate can also be applied to the substrate in solution.

Suitable solvents include, for example, water, ethanol, methanol, methyl ethyl ketone, diethyl ether, dioxane, hexane, heptane, benzene, toluene, chloroform, methylene chloride, tetrahydrofuran and acetonitrile.

The solution of the polymer obtained by polymerization of tert-butylaminoethyl methacrylate is applied to the standard polymers, for example, by dipping, spraying or painting.

If the polymer is produced directly on the substrate surface without grafting, suitable initiators are added in order to promote polymerization. Initiators which can be used include, inter alia, azonitriles, alkyl peroxides, hydroperoxides, acyl peroxides, peroxoketones, peresters, peroxocarbonates, peroxodisulfate, persulfate and all the customary photoinitiators, such as, for example, acetophenones and benzophenone.

The initiation of the polymerization can be carried out by means of heat or by electromagnetic radiation, such as, for example, UV light or γ-radiation.

The present antimicrobial polymers can be used for the production of products such as medical articles or hygienic articles.

Medical articles produced by the process of the invention include, for example, catheters, blood bags, drainages, guide wires and surgical instruments.

The process according to the invention can furthermore be employed for the production of hygienic articles, such as, for example, toothbrushes, toilet seats, combs and packaging materials.

Having now generally described this invention, a further understanding can be obtained by reference to certain specific examples which are provided herein for purposes of illustration only and are not intended to be limiting unless otherwise specified.

Example 1

A 27 g amount of tert-butylaminoethyl methacrylate and 150 ml of ethanol is heated to 65° C. under an inert gas. When the temperature is reached, 0.37 g of azobisisobutyronitrile, dissolved in 10 ml of methyl ethyl ketone, is added. At the end of 24 hours, the reaction is ended by stirring the mixture into 1 l of a water/ice mixture. The reaction product is removed by filtration and washed with 300 ml of n-hexane. The product is then distributed over several Soxhlets and extracted with water for 24 hours, and is then dried at 50° C. in vacuo for 12 hours.

Example 2

A 4 g amount of poly-tert-butylaminoethyl methacrylate from Example 1 is dissolved in 40 ml of tetrahydrofuran. A polyamide 12 film is immersed in this solution for 5 seconds, removed from the solution for 10 seconds and them immersed again for 5 seconds, so that a uniform film of poly-tert-butylaminoethyl methacrylate has formed on the polyamide film after subsequent drying at room temperature under normal pressure. The film is then dried at 50° C. in vacuo for 24 hours. The film is subsequently extracted in water at 30° C. 5 times for 6 hours and then dried at 50° C. for 12 hours.

Example 3

A 4 g amount of poly-tert-butylaminoethyl methacrylate from Example 1 is dissolved in 40 ml of tetrahydrofuran. A polyvinyl chloride film is immersed in this solution for 2 seconds, removed from the solution for 10 seconds and then immersed again for 2 seconds, so that a uniform film of poly-tert-butylaminoethyl methacrylate has formed on the polyvinyl chloride film after subsequent drying at room temperature under normal pressure. The film is then dried at 50° C. in vacuo for 24 hours. The film is subsequently extracted in water at 30° C. 5 times for 6 hours and then dried at 50° C. for 12 hours.

Example 4

A polyamide 12 film is exposed to the 172 nm radiation of an Excimer radiation source manufactured by Heraeus for 2 minutes under a pressure of 1 mbar. The film activated in this way is laid and fixed in an irradiation reactor under an inert gas. The film is then covered with a layer of 20 ml of a mixture of 3 g of tert-butylaminoethyl methacrylate and 97 g of methanol in a countercurrent flow of inert gas. The irradiation chamber is closed and placed at a distance of 10 cm underneath an Excimer radiation unit manufactured by Heraeus, which has an emission of wavelength 308 nm. The irradiation is started, and the exposure time is 15 minutes. The film is removed and rinsed off with 30 ml of methanol. The film is then dried at 50° C. in vacuo for 12 hours. The film is subsequently extracted in water at 30° C. 5 times for 6 hours and then dried at 50° C. for 12 hours.

Measurement of Bactericidal Action

The bactericidal action of coated plastics was measured as follows:

A 100 µl of a cell suspension of Klebsiella pneumoniae was placed on a piece of film 2×2 cm in size. The bacteria were suspended in PBS buffer (phosphate-buffered saline); the cell concentration was $10^5$ cells per ml of buffer solution. This drop was incubated for up to 3 hours. In order to prevent any drying out of the applied drop, the piece of film was laid in a polystyrene Petri dish wetted with 1 ml of water. After the end of the contact time, the 100 µl were taken up with an Eppendorf tip and diluted in 1.9 ml of sterile PBS. A 0.2 ml amount of this solution was plated out on nutrient agar. The rate of inactivation was calculated from the number of colonies which had grown.

Checking the Resistance of the Coatings

Before the measurement of the bactericidal action, the coated films were subjected to the following pretreatments:

A: Washing in boiling water for 10 minutes
B: Washing in 96% strength ethanolic solution for 10 minutes
C: Washing in warm water at 25° C. under ultrasonic treatment for 10 minutes
D: No pretreatment The results of the measurements, taking into account the particular pretreatment are listed in Table 1.

TABLE 1

| Example | Rate of Inactivation | | | |
|---|---|---|---|---|
| | A | B | C | D |
| 2 | 4% | <10% | 56% | 99.9% |
| 3 | 5% | <10% | 54% | 99.9% |
| 4 | 99.9% | 99.9% | 99.9% | 99.9% |

After thermal, chemical or mechanical pretreatment, the antimicrobial layers produced by grafting of a substrate surface continue to show virtually complete inactivation of the bacteria applied. The physically adhered layers are less stable to the pretreatment of methods A, B and C.

In addition to the microbicidal activity against cells of Klebsiella pneumoniae which has been described above, all the coated films also showed a microbicidal action against cells of Pseudomonas aeruginosa, Staphylococcus aureus, Escherichia coli, Rhizopus oryzae, Candida tropicalis and Tetrahymena pyriformis. The rate of inactivation after treatment method D was also more than 99% in these cases.

The disclosure of priority German Application No. 197 09 076.1 having a filing date of Mar. 6, 1997 is hereby incorporated by reference into the application.

Obviously, numerous modifications and variations of the present invention are permissible in light of the above teachings. It is, therefore, to be understood that within the scope of the appended claims, the invention may be practiced otherwise than as specifically described herein.

What is claimed as new and desired to be secured by Letters Patent of the United States is:

1. A method of imparting antimicrobial activity to the surfaces of an apparatus or article, which comprises:
    polymerizing a monomer material consisting of tert-butylaminoethylmethacrylate to prepare poly(tert)-butylaminoethylmethacrylate, without grafting the polymer onto the surface(s) of said apparatus or article, thereby imparting antimicrobial activity to the surface (s) of said apparatus or article.

2. The method as claimed in claim 1, wherein said apparatus or article provided with antimicrobial activity is a medical article.

3. The method as claimed in claim 1, wherein said apparatus provided with antimicrobial activity is a hygienic article.

4. The method as claimed in claim 1, wherein said apparatus or article is manufactured of a material selected from the group consisting of polyurethane, polyamide, polyester, polyether, polyether-block amides, polystyrene, polyvinyl chloride, polycarbonate, polyorganosiloxanes, polyolefins, polysulfones, polyisoprene, polychloroprene, polytetrafluoroethylene, blends of these polymers and natural or synthetic rubber.

5. The method as claimed in claim 1, wherein the poly-tert-butylaminoethylmethacrylate is applied to said surface (s) by contact of said surface(s) with a solution containing tert-butylaminoethylmethacrylate in a concentration ranging from 1 to 10% by weight and polymerizing the monomer thereby applying the resulting polymer to said surface(s).

* * * * *

UNITED STATES PATENT AND TRADEMARK OFFICE
CERTIFICATE OF CORRECTION

PATENT NO. : 6,316,044 B2
DATED : November 13, 2001
INVENTOR(S) : Ottersbach et al.

It is certified that error appears in the above-identified patent and that said Letters Patent is hereby corrected as shown below:

<u>Title page,</u>
Item [45] and the Notice information should read:

-- (45) Date of Patent: *Nov. 13, 2001 --

-- (*) Notice: This Patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Item [75], the Inventors should read:

-- [75] Inventors: Peter Ottersbach, Windeck; Frank Hill, *deceased,* late of Mettmann, by Hella Luise Hill, heiress, Mettmann; Henning Hinrich Hill, heir, Mettmann; Freidrich Frank Hill, heir, Waldsee; Regina Luise Hill, heiress, Speyer; Christine Anders, Haltern, all of (DE) --

Signed and Sealed this

Eighteenth Day of June, 2002

*Attest:*

*Attesting Officer*

JAMES E. ROGAN
*Director of the United States Patent and Trademark Office*